United States Patent [19]
Whiting et al.

[11] Patent Number: 5,457,728
[45] Date of Patent: * Oct. 10, 1995

[54] CORONARY TRACKING DISPLAY

[75] Inventors: James S. Whiting, Los Angeles; Neal L. Eigler, Woodland Hills, both of Calif.

[73] Assignee: Cedars-Sinai Medical Center, Los Angeles, Calif.

[*] Notice: The portion of the term of this patent subsequent to Oct. 1, 2008, has been disclaimed.

[21] Appl. No.: 771,015

[22] Filed: Sep. 30, 1991

Related U.S. Application Data

[63] Continuation-in-part of Ser. No. 614,790, Nov. 14, 1990, Pat. No. 5,054,045.

[51] Int. Cl.$^6$ ..................................................... H05G 1/64
[52] U.S. Cl. .......................................... 378/98.2; 378/98.3
[58] Field of Search ................................. 378/99; 358/111

[56] References Cited

U.S. PATENT DOCUMENTS

| | | | |
|---|---|---|---|
| 4,674,107 | 6/1987 | Urban et al. | 378/99 |
| 4,937,848 | 6/1990 | Horbaschek et al. | 378/99 |
| 5,054,045 | 10/1991 | Whiting et al. | 378/99 |

Primary Examiner—Craig E. Church
Attorney, Agent, or Firm—Lyon & Lyon

[57] ABSTRACT

A method of displaying details of a coronary artery lesion in a cineangiogram, by adjusting each frame of the cineangiogram so that the lesion is continually displayed at a fixed location on a display. The remaining cardiac anatomy appears to move, in background, past a stationary arterial segment, thus making the displayed arterial segment easier to identify and to examine by medical personnel. Cineangiographic image frames are digitized and processed by a processor and the image frames are digitally shifted to place the arterial segment in substantially the same viewing location in each frame. Sequential image frames may be presented to the viewer as a stereoscopic pair, to produce pseudostereopsis. The arterial segment appears to the viewer in foreground, as if it was floating in front of the remaining cardiac anatomy. Image frames may be further processed to aid examination by medical personnel. The processor may make quantitative measurements of the cineangiogram and may display results of those measurements to aid review of the cineangiogram. Frames may be averaged to reduce quantum noise and to blur any structure noise; frames may be compared with prior cineangiograms to increase clarity or contrast. Coordinate adjustments for a cineangiogram may help guide therapeutic procedures, or may help enhance other imaging procedures such as fluoroscopy.

32 Claims, 1 Drawing Sheet

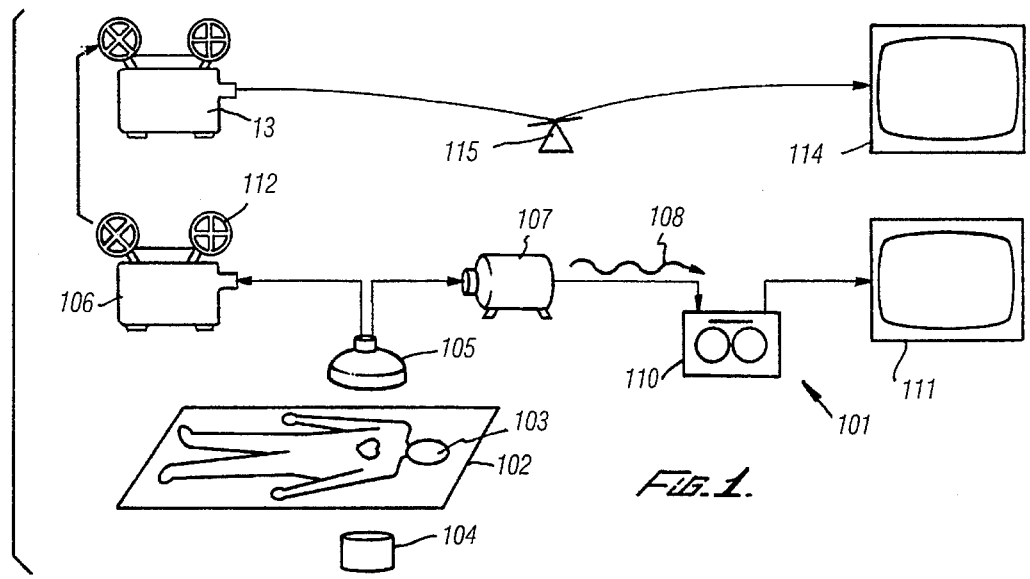
Fig. 1.
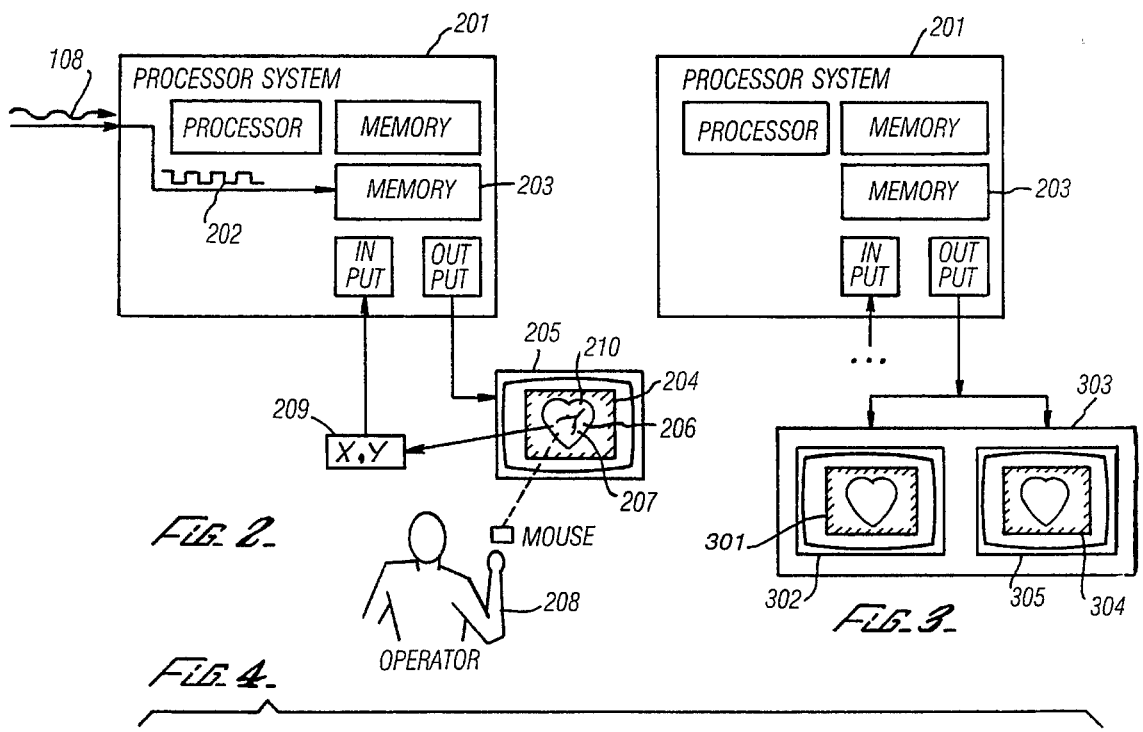
Fig. 2.
Fig. 3.
Fig. 4.

CORONARY TRACKING DISPLAY

CROSS-REFERENCE TO RELATED APPLICATION

This application is a continuation-in-part of application Ser. No. 07/614,790, filed Nov. 14, 1990 now U.S. Pat. No. 5,054,045 in the name of the same inventors and with the same title, hereby incorporated by reference as if fully set forth herein.

BACKGROUND OF THE INVENTION

1. Field of the Invention

This invention relates to a coronary tracking display. More specifically, this invention relates to a coronary tracking display which improves visibility of details of coronary artery lesions in cineangiography.

2. Description of Related Art

Cineangiography for coronary arterial segments is typically done by means of an x-ray image. An artery is filled with a contrast material (for example, a large molecule with iodine in it, such as megluamine diatrozoate (sold under the name Renografin 76) or iohexal (sold under the name Omnipaque), and its arterial segments are examined. Medical personnel may examine the shape of the inner wall of the artery and look for space where the contrast material would be expected to fill, but does not. These spaces are called "filling defects" and commonly indicate lesions for which a specific treatment may be desireable.

It is advantageous to collect and display images of coronary arterial segments for later review by medical personnel. For example, review of such images may prove useful in detecting and locating lesions, and thus may assist in treatment of a patient by interventional methods. However, one problem which has arisen in the art is that image quality under conditions imposed by cineangiography may be poor, making it difficult for medical personnel to readily recognize critical features.

It may also be advantageous to insert a catheter into an artery, approach an arterial segment containing a lesion, and perform an interventional therapy on that lesion. For example, a lesion may be dilated with a balloon or ablated with a laser. Because these treatments may have adverse effects, it is desireable to identify which lesions truly require treatment.

Another problem which has arisen in the art is that it may be difficult to move such a catheter within the patient's arterial network. It would be advantageous to superimpose an image of the catheter on the patient's arterial network while moving the catheter. However, the contrast material may have adverse effects on the patient, so it is generally not preferred to collect and display cineangiographic images while moving a catheter.

SUMMARY OF THE INVENTION

The invention provides a method of displaying details of a coronary artery lesion in a cineangiogram, by (digitally or analog) adjusting each frame of the cineangiogram so that the lesion is continually displayed at a fixed location on a display. As a result, the remaining cardiac anatomy appears to move, in background, past a stationary arterial segment, thus making the displayed arterial segment easier to identify and to examine by medical personnel. In a preferred embodiment, cineangiographic image frames are digitized and processed by a processor and the image frames are digitally shifted to place the arterial segment in substantially the same viewing location in each frame.

In a preferred embodiment, sequential image frames may be presented to the viewer as a stereoscopic pair, to produce pseudostereopsis. As a result, the arterial segment appears to the viewer in foreground, as if it was floating in front of the remaining cardiac anatomy. Moreover, image frames may be further processed to aid examination by medical personnel. The processor may make quantitative measurements of the cineangiogram and may display results of those measurements to aid review of the cineangiogram. Frames may be averaged to reduce quantum noise and to blur any structure noise; frames may be compared with prior cineangiograms to increase clarity or contrast. Coordinate adjustments for a cineangiogram may help guide therapeutic procedures, or may help enhance other imaging procedures such as fluoroscopy.

BRIEF DESCRIPTION OF THE DRAWINGS

FIG. 1 shows a drawing of a cineangiographic system.

FIG. 2 shows a block diagram of a digital processing system for adjusting the image of the lesion in a cineangiogram.

FIG. 3 shows a block diagram of a digital processing system for producing pseudostereopsis.

FIG. 4 shows a block diagram and drawing of a cineangiographic system being employed to aid in catheterization.

DESCRIPTION OF THE PREFERRED EMBODIMENT

FIG. 1 shows a drawing of a cineangiographic system.

A cineangiographic system 101 may comprise a table 102 on which a patient 103 is placed, with an x-ray generating tube 104 below the table 102 for projecting x-rays and an x-ray intensifier tube 105 placed above the table for receiving x-rays. The x-ray intensifier tube 105 may be coupled to a motion-picture camera 106 or a television camera 107, which may produce a video image signal 108 of the patient's heart 109, as is well known in the art. The video image signal 108 may be stored on a storage medium such as a videotape 110, and may later be retrieved and displayed on a video monitor 111 for review by medical personnel, as is well known in the art.

A film 112 captured by the motion-picture camera 106 may also be displayed by a motion-picture projector 113 on a projection screen 114. The film image may be directed by the motion-picture projector 113 at an adjustable mirror 115, which may be disposed to reflect the film image onto the projection screen 114.

FIG. 2 shows a block diagram of a digital processing system for adjusting the image of the lesion in a cineangiogram.

In a preferred embodiment, the video image signal 108 may be coupled to a processor system 201, which may digitize the video image signal 108 and store a digital signal 202 in a memory 203. The processor system 201 may then adjust each frame of the cineangiogram so that a lesion is continually displayed at a fixed location on a display screen.

In a preferred embodiment, the processor system 201 may comprise a processor, memory comprising a stored program, memory comprising data, and input/output devices, as is well known in the art. Although the operation of the processor system 201 is given in terms of functions that it performs, it would be clear to one of ordinary skill in the art, after perusal of the specification, drawings and claims herein, that modification and/or programming of a standard microprocessor to achieve the functions disclosed herein would be a straightforward task and would not require undue experimentation.

In a preferred embodiment, the processor system 201 may comprise an ADAC computer made by ADAC Corporation, or may be a GE DXC image acquisition system made by General Electric Corporation.

COLLECTING DATA ON LESION LOCATION

In a preferred embodiment, the processor system 201 may operate interactively with a human operator, as is well known in the art. First, the processor system 201 may retrieve a single frame 204 of the stored digital signal 202 from memory 203, and may display that frame 204 on an operator's monitor 205. As each frame 204 is displayed, the cineangiogram will show a motion picture of the patient's heart 109. In this motion picture, an arterial segment 206 may appear on which there is a lesion 207. However, because of the patient's heartbeat, the lesion 207 will tend to move about on the screen.

A human operator 208 may examine the operator's monitor 205 and may indicate (e.g., with a pointing device such as a light pen, mouse or trackball) the location in the frame 204 of the lesion 207. The processor system 201 may receive the indication by the operator 208 and may store a set of spatial coordinates 209 for the lesion 207 which it associates with the frame 204. The processor system 201 may then repeat this interactive process for each frame 204 of the stored digital signal 202. When complete, the processor system 201 will have a record stored in memory 203 of movements which the lesion 207 undergoes as a result of the patient's heartbeat.

In an alternative preferred embodiment, the processor system 201 may locate the lesion 207 by edge-detection or other automatic means. For example, the stored digital signal 202 may comprise a set of pixels, each of which represents a measure of light level detected by the television camera 107. The patient's arterial network may have a different light level from other structure. The processor system 201 may then trace the patient's arterial network and determine what areas of the digital signal 202 represent arteries and what areas represent other structure.

In a preferred embodiment, the technique used by the processor system 201 for edge-detection may comprise a technique based on an optimum matched filter, described in a technical appendix to this application and hereby incorporated by reference as if fully set forth herein. A description of a preferred optimum matched filter technique is also given in the Ph.D. thesis of J. Martin Pfaff, on file with the UCLA Library System, and hereby incorporated by reference as if fully set forth herein. However, it would be clear to one of ordinary skill in the art, after perusal of the specification, drawings and claims herein, that other techniques for edge-detection or for otherwise locating the lesion 207 would be workable, and are within the scope and spirit of the invention.

In one aspect of this alternative preferred embodiment, the operator 208 may identify the lesion 207 in one frame 204 by the same technique, but the processor system 201 may determine the location of the lesion 207 in the succeeding frames 204 automatically. For example, the processor system 201 may locate the lesion 207 by noting the distance from the lesion 207 to a reference point 210, such as a junction of arterial segments, and by locating the lesion 207 in the succeeding frames 204 by reference to the reference point 210.

In another aspect of this alternative preferred embodiment, the processor system 201 may determine the location of the lesion 207 by noting a point in the arterial segment where the arterial segment is much narrower. In this aspect, the operator 208 may identify the lesion 207 of interest out of several possible lesions 207 which might be displayed.

Where the cineangiogram is captured on film 112, the operator 208 may examine the projection screen 114 and may indicate (e.g., with a pointing device such as an acoustical x-y digitizer) the location on the projection screen 114 of the lesion 207 in each frame 204 of the cineangiogram (prior to adjustment). The processor system 201 may receive the indication by the operator 208 and may store the set of spatial coordinates 209 for the lesion 207 which it associates with the frame 204. The processor system 201 may then repeat this interactive process for each frame 204 of the film 112. When complete, the processor system 201 will have a record stored in memory 203 of that motion which the lesion 207 undergoes as a result of the patient's heartbeat.

FURTHER IMAGE PROCESSING

In a preferred embodiment, the processor system 201 may further process the frames 204, both to aid visual examination by medical personnel and to generate medical data.

The processor system 201 may compute quantitative measurements of the cineangiogram. For example, edge detection and centerline detection allow the processor system 201 to measure or compute the length, width and spatial orientation of arterial segments 206, size and location of lesions 207 or other morphologies of the arterial segments 206, and relative stenosis. The processor system 201 may also compute roughness index, cross-sectional area and thickness of arterial segments 206, by methods which are well known in the art. Because data on lesion 207 location is collected, the processor system 201 generally need not recompute the location of the arterial segment 206 in each frame 204, aiding automated quantitative measurement.

Image enhancement techniques may be applied to the video image signal 108 and the frames 204 altered so as to enhance their clarity. For example, the processor system 201 may locate the edges of arterial segments 206, or other features such as the location and size of lesions 207, and may superimpose them on the video monitor 111 when displaying the frames 204. The processor system 201 may display quantitative measurements as "false color" on the video monitor 111.

In a preferred embodiment, the frames 204 may be averaged to reduce quantum noise and to blur any structure noise, either for display or when computing quantitative measurements of the cineangiogram. In a preferred embodiment, after adjusting each frame 204 of the cineangiogram so that the lesion 207 is continually found at a fixed location, the processor system 201 may average the adjusted frames 204 and compute quantitative measurements on the average. The average may be over a cardiac cycle of about thirty frames 204. In an alternative preferred embodiment, the processor system 201 may compute quantitative measurements for each frame 204 and average the quantitative measurements over a cardiac cycle.

In a preferred embodiment, the frames 204 may also be processed to increase contrast, either for display or when computing quantitative measurements of the cineangiogram. In a preferred embodiment, these steps may be performed:

(1) A first cineangiogram may be taken, with contrast material present, and each frame 204 adjusted based on the set of spatial coordinates 209 which are collected for the lesion 207.

(2) A second cineangiogram is taken, this time without contrast material present, and each frame 204 adjusted based on the set of spatial coordinates 209 collected for the lesion 207 in the first cineangiogram.

(3) Each frame 204 of the second cineangiogram is subtracted, after adjustment, from a corresponding frame 204 of the first cineangiogram, or from a corresponding frame 204 of a third cineangiogram taken with contrast material present. Alternatively, the frames 204 of the second cineangiogram may be averaged, after adjustment, over a cardiac cycle, and the average subtracted from every frame 204 of the first cineangiogram.

It would be clear to one of ordinary skill in the art, after perusal of the specification, drawings and claims herein, that other and further signal processing may be performed on the stored digital signal 202, such as filtering, noise-removal and other related techniques. Such other and further signal processing would be workable, and is within the scope and spirit of the invention.

DISPLAYING THE LESION

The processor system 201 may then display the stored digital signal 202 on the video monitor 111 for review by medical personnel. First, the processor system 201 may retrieve a single frame 204 from memory 203, and note the spatial coordinates 209 of the lesion 207. The processor system 201 may then adjust that frame 204 to place the lesion 207 in a specified location (e.g., a position near the center of the screen). Alternatively, the processor system 201 may adjust each frame 204 except the first to place the lesion 207 in the same location as in the first frame 204. As a result, the lesion 207 appears in the same location in each screen, and the remaining cardiac anatomy appears to move, in background, past a stationary arterial segment.

The processor system 201 may also display the cineangiogram, as captured on film 112, on the projection screen 114. The processor system 201 may be coupled to the mirror 115 and may continually adjust the position of the mirror 115 so as to continually adjust the reflection of the film image onto the projection screen 114. In particular, the processor system 201 may adjust the position of the mirror 115 so that the lesion 207 appears in the same location on the projection screen 114 in each frame of the film 112, in like manner as if a digital frame image had been adjusted so that the lesion 207 appears in the same location in each frame 204.

PSEUDOSTEREOPSIS

FIG. 3 shows a block diagram of a digital processing system for producing pseudostereopsis.

In a preferred embodiment, the processor system 201 may present a pair of sequential frames 204 to medical personnel as a stereoscopic pair, to produce pseudostereopsis. An odd frame 301 is displayed on a left half 302 of a stereoscopic display 303, while an even frame 304 is displayed on a right half 305 of the stereoscopic display 303. When the stereoscopic display 303 is viewed with appropriate stereoscopic equipment, a three-dimensional image will appear, as is well known in the art. As a result, the arterial segment appears to the viewer in foreground, as if it was floating in front of the remaining cardiac anatomy.

AID IN CATHETERIZATION

FIG. 4 shows a block diagram and drawing of a cineangiographic system being employed to aid in catheterization.

In a preferred embodiment, a catheter patient 401 may be catheterized with a catheter 402 which is inserted into one of the patient's arteries (typically the femoral artery), as is well known in the art. In a preferred embodiment, the catheter patient 401 may be positioned on a fluoroscope 403, which generates an x-ray image 404 of the catheter 402. The x-ray image 404 may then be superimposed on a frame 204 retrieved from memory 203 by the processor system 201, to form a composite image 405. The composite image 405 may then be adjusted so that the catheter remains in the same location in the image.

For example, the processor system 201 may simply "play back" the set of coordinate adjustments it made for the cineangiogram, applying those same coordinate adjustments to the x-ray image 404 of the catheter 402. In this aspect of the invention, movement of the image which is due to the patient's heartbeat may be essentially eliminated, so that medical personnel performing the catheterization may determine routing of the catheter in the patient's arterial network.

In like manner, coordinate adjustments recorded for the cineangiogram may help guide other therapeutic procedures, such as balloon angioplasty, laser angioplasty, atherectomy, stent insertion, thrombectomy, intravascular ultrasound, radiation therapy and pharmacologic agent delivery. In general, when invading the body with a moving object, the progress of that object may be viewed by means of images which are adjusted by the techniques described herein, so that progress of the moving object may be measured with reference to a relatively fixed map of the patient's body. In a preferred embodiment, these steps may be performed:

(1) A first cineangiogram may be taken, with contrast material present, and each frame 204 adjusted based on the set of spatial coordinates 209 which are collected for the lesion 207. Image enhancement techniques may be applied to enhance the clarity of the position of the arterial segment 206 and the lesion 207.

(2) A therapeutic process may be performed with a live second cineangiogram, this time without contrast material present. It may be quite difficult to see the arterial segment 206 or the lesion 207 in the second cineangiogram, so the results of image enhancement from the first cineangiogram are used to identify them. In a preferred embodiment, each frame 204 of the second cineangiogram may be adjusted based on the set of spatial coordinates 209 collected during the first cineangiogram. In a preferred embodiment, the patient's electrocardiogram may be used to synchronize the spatial coordinates 209 from the first cineangiogram with the frames 204 in the second cineangiogram. In a preferred embodiment, the processor system 201 may indicate the edges of arterial segments 206, or other features such as the location and size of lesions 207, and may superimpose them on the video monitor 111 when displaying the frames 204, as a "roadmap" for the therapeutic process.

In a preferred embodiment, steps (1) and (2) may be alternated in sequence, so that a first cineangiogram is taken, then the therapeutic process is advanced some using the results of image enhancement, then another first cineangiogram is taken, then the therapeutic process is advanced some more using the results of further image enhancement, and so on.

OTHER MEDICAL IMAGING APPLICATIONS

It would be clear to one of ordinary skill in the art, after perusal of the specification, drawings and claims herein, that the techniques described herein for cineangiograms may also be applied to fluoroscopy. In the art of fluoroscopy, an x-ray generating tube (like the x-ray generating tube 104 of the cineangiographic system 101) may be disposed for projecting x-rays and an x-ray intensifier tube (like the x-ray intensifier tube 105 of the cineangiographic system 101) may be disposed for receiving x-rays. The x-ray intensifier tube 105 may be coupled to a display (like the video monitor 111 of the cineangiographic system 101) for immediate display of an x-ray image of the patient 103.

One problem which has arisen in the art of fluoroscopy is that excessive exposure to x-rays can put both the patient 103 and any nearby medical personnel (such as those viewing the x-ray image) at risk of radiation damage. One solution has been to generate a sequence of relatively still x-ray images, each using only relatively short bursts of x-rays, at a display rate which gives the illusion of a continuous motion picture, i.e., an x-ray movie similar to a cineangiogram. It would be advantageous to reduce exposure to x-rays, e.g., by reducing the number of frames per second which are generated and displayed ("frame rate"). However, because of the patient's heartbeat, this has the effect of producing an x-ray image which is jumpy and difficult to view.

Each frame of the fluoroscopic x-ray image may be adjusted by the techniques shown herein, so that an identified feature (e.g. an arterial segment or lesion) is continually displayed at a fixed location on the display screen. Because the identified feature does not move about on the screen, jumpiness which might be induced by a lowered frame rate is ameliorated and the image is of acceptable quality. Accordingly, the frame rate may be reduced from about 30 frames per second to about 3 frames per second or fewer, while maintaining acceptable visualization of the arterial segment or lesion.

It would be clear to one of ordinary skill in the art, after perusal of the specification, drawings and claims herein, that the techniques described herein for cineangiograms may also be applied to other medical imaging applications, including imaging applications which use imaging signals other than x-rays. For example, the techniques described herein may also be applied to echocardiography (of several types, such as exercise, transesophageal, transthoracic, intravascular ultrasound), ultrafast computed tomography, cine magnetic resonance imaging, and single-photon emission computed tomography. In general, a sequence of images comprising a moving feature may be adjusted by the techniques described herein to continually maintain the moving feature at a relatively fixed location in the image, and the adjusted image may be used by personnel or processes which find advantage to looking to a relatively fixed location for the moving feature.

ALTERNATIVE EMBODIMENTS

While preferred embodiments are disclosed herein, many variations are possible which remain within the concept and scope of the invention, and these variations would become clear to one of ordinary skill in the art after perusal of the specification, drawings and claims herein.

We claim:

1. A system for displaying a segment of a coronary artery in a first cineangiogram, comprising means for adjusting each frame of a second cineangiogram so that the segment is continually displayed at a substantially fixed location on a display screen in response to a set of adjustments for each said frame; and means for adjusting each frame of said first cineangiogram in response to said set of adjustments for each said frame of said second cineangiogram.

2. A system as in claim 1, comprising means for comparing at least one frame of said first cineangiogram with at least one corresponding frame of said second cineangiogram.

3. A system as in claim 1, comprising means for subtracting at least one frame of said first cineangiogram from at least one corresponding frame of said second cineangiogram.

4. A system as in claim 1, comprising means for computing an average of a plurality of frames of said first cineangiogram; and means for subtracting said average from at least one frame of said second cineangiogram.

5. A system as in claim 1, comprising means for computing an image enhancement in response to said second cineangiogram; and means for enhancing at least one frame of said first cineangiogram in response to said image enhancement.

6. A system as in claim 1, comprising means for computing a location of at least one arterial segment in response to said second cineangiogram; and means for superimposing an indicator of said location on at least one frame of said first cineangiogram.

7. A system for displaying a segment of a coronary artery in a cineangiogram, comprising means for digitizing cineangiogram image frames;

means for locating an arterial segment in said image frames; and means for digitally shifting said image frames to place the arterial segment in substantially the same viewing location in each one of said image frames.

8. A system as in claim 7, wherein said means for locating comprises means for displaying at least one of said image frames to an operator; and means for retrieving information indicating a location of said arterial segment from said operator.

9. A system as in claim 7, comprising means for edge detection.

10. A system as in claim 7, comprising means for presenting sequential image frames to a viewer as a stereoscopic pair.

11. A system as in claim 7, comprising means for further processing image frames to aid examination by a viewer.

12. A system as in claim 7, comprising means for averaging a plurality of said frames.

13. A system as in claim 12, comprising means for computing a measure of vessel cross-section in response to said means for averaging.

14. A system for displaying a segment of a coronary artery in a cineangiogram, comprising means for identifying said segment in a plurality of frames of said cineangiogram; and means for adjusting a display position of each of said frames so that said segment is placed in substantially the same viewing location in each of said frames.

15. A system for displaying a segment of a coronary artery in a cineangiogram, comprising means for identifying said segment in a plurality of frames of said cineangiogram;

means for adjusting a display position of each of said frames so that said segment is placed in substantially the same viewing location in each of said frames; and means for displaying each of said frames in its adjusted display position.

16. A system as in claim 15, wherein said frames comprise digital image frames.

17. A system as in claim 15, wherein said means for identifying comprises means for displaying at least one of said image frames to an operator; and means for retrieving information indicating a location of said arterial segment from said operator.

18. A system as in claim 15, comprising means for edge-detection.

19. A method of displaying a segment of a coronary artery in a first cineangiogram, comprising the steps of adjusting each frame of a second cineangiogram so that the segment is continually displayed at a substantially fixed location on a display screen in response to a set of adjustments for each said frame; and adjusting each frame of said first cineangiogram in response to said set of adjustments for each said frame of said second cineangiogram.

20. A method as in claim 19, comprising the step of comparing at least one frame of said first cineangiogram with at least one corresponding frame of said second cineangiogram.

21. A method as in claim 19, comprising the step of subtracting at least one frame of said first cineangiogram from at least one corresponding frame of said second cineangiogram.

22. A method as in claim 19, comprising the steps of computing an average of a plurality of frames of said first cineangiogram; and subtracting said average from at least one frame of said second cineangiogram.

23. A method as in claim 19, comprising the steps of computing an image enhancement in response to said second cineangiogram; and enhancing at least one frame of said first cineangiogram in response to said image enhancement.

24. A method as in claim 19, comprising the steps of computing a location of at least one arterial segment in response to said second cineangiogram; and superimposing an indicator of said location on at least one frame of said first cineangiogram.

25. A method as in claim 24, comprising the step of repeatedly alternating said steps of computing and superimposing.

26. A method as in claim 19, comprising the step of repeatedly alternating said steps of adjusting each frame of said first and second cineangiograms.

27. A system for moving a catheter in a patient, comprising means for producing an image of said catheter in said patient's body in a plurality of frames;

means for adjusting a display position of each of said frames so that said image of said catheter is placed in substantially the same viewing location in each of said frames; and means for displaying each of said frames in its adjusted display position.

28. A system as in claim 27, wherein said image of said catheter is an x-ray image.

29. A system as in claim 27, comprising means for determining a set of adjustments to be applied to a first plurality of frames, based on a location of an arterial segment in a second plurality of frames; and means for applying said set of adjustments to said display position of said image of said catheter.

30. A system for displaying a segment of a coronary artery in a cineangiogram having a plurality of frames, comprising means for directing at least one said frame at a mirror disposed to reflect said frame onto a display; and means for adjusting a position of said mirror so that said at least one frame is reflected onto an adjusted location on said display.

31. A method of displaying a segment of a coronary artery in a cineangiogram, comprising the step of adjusting each frame of the cineangiogram so that the segment is continually displayed at a substantially fixed location on a display screen.

32. A method as in claim 31, wherein said step of adjusting comprises the steps of directing said frame at a mirror disposed to reflect said frame onto a display; and adjusting a position of said mirror so that said frame is reflected onto an adjusted location on said display.

* * * * *

UNITED STATES PATENT AND TRADEMARK OFFICE
CERTIFICATE OF CORRECTION

PATENT NO. : 5,457,728  
APPLICATION NO. : 07/771015  
DATED : October 10, 1995  
INVENTOR(S) : Whiting et al.

Page 1 of 1

It is certified that error appears in the above-identified patent and that said Letters Patent is hereby corrected as shown below:

In column 1, under the "Cross-Reference to Related Applications" section but before the "Background of the Invention" section, please insert the following:

--FEDERAL SUPPORT  
The U.S. Government has a paid-up license in this invention and the right in limited circumstances to require the patent owner to license others on reasonable terms as provided for by the terms of Grant No. R01HL42997-01A1 awarded by the National Institutes of Health.--

Signed and Sealed this

Second Day of June, 2009

JOHN DOLL  
*Acting Director of the United States Patent and Trademark Office*